(12) United States Patent
Lee et al.

(10) Patent No.: US 8,225,674 B2
(45) Date of Patent: Jul. 24, 2012

(54) TENSILE TESTING DEVICE

(75) Inventors: Feng-Chi Lee, Taipei (TW); Kuo-Chuan Chiu, Taipei (TW)

(73) Assignee: Cheng Uei Precision Industry Co., Ltd., Taipei (TW)

( * ) Notice: Subject to any disclaimer, the term of this patent is extended or adjusted under 35 U.S.C. 154(b) by 252 days.

(21) Appl. No.: 12/831,449

(22) Filed: Jul. 7, 2010

(65) Prior Publication Data

US 2012/0006126 A1    Jan. 12, 2012

(51) Int. Cl.
*G01N 3/08* (2006.01)

(52) U.S. Cl. ............................................ 73/826; 73/760

(58) Field of Classification Search .................... 73/760, 73/826, 831
See application file for complete search history.

(56) References Cited

U.S. PATENT DOCUMENTS

| 4,231,248 | A  | * | 11/1980 | Rolinski et al. ................. 374/49 |
| 4,794,805 | A  | * | 1/1989 | Carney et al. ............ 73/862.452 |
| 5,431,060 | A  | * | 7/1995 | Lauren ............................. 73/831 |
| 7,749,247 | B2 | * | 7/2010 | Tegg ............................... 606/213 |
| 2001/0001371 | A1 | * | 5/2001 | Arrington et al. .............. 73/835 |

* cited by examiner

*Primary Examiner* — Max Noori
(74) *Attorney, Agent, or Firm* — WPAT, P.C.; Anthony King

(57) ABSTRACT

A tensile testing device includes a supporting unit, a cantilever unit and a connecting unit. The supporting unit defines a plurality of mating elements secured thereon for mating with a detected element. The cantilever unit is connected with the detected element by a lead for reading the tension. The connecting unit includes a penal attached on a lateral surface of the supporting unit, a turning plate pivotally installed on a front surface of the panel and rotated around a first axis which is perpendicular to the lateral surface, a first connecting block fastened to a front surface of the turning plate, and a second connecting block of which rear end pivotally connects the first connecting block and turns around a second axis perpendicular to the first axis.

17 Claims, 8 Drawing Sheets

TENSILE TESTING DEVICE

BACKGROUND OF THE INVENTION

1. Field of the Invention

The present invention relates to a tensile testing device, and in particular to a tensile testing device which can detect a tension in that a plug element is pulled out from a mating element in multi-direction.

2. The Related Art

During designing and manufacturing electronic or mechanical products, such as plug element, it is of vital importance to detect a tension in that a plug element is pulled out from a mating element and to control the tension in a reasonable range.

As shown in FIG. 8, a conventional tensile testing device 1' is used for detecting a tension in that a plug element is pulled out from a mating element. The tensile testing device 1' includes a supporting unit 10', a cantilever unit 30' and a connecting unit 20' connecting the supporting unit 10' and the cantilever unit 30'. A mating element 3' is secured on the supporting unit 10' and is adjacent to a front surface of the supporting unit 10', with a mating socket opening forward. The plug element 2' is plugged in the mating element 3' and is connected with the cantilever unit 30' by a lead 4'. The connecting unit 20' is substantial L-shaped, and has a first connecting block 21' and a second connecting block 22' perpendicularly connecting the first connecting block 21'. A free end of the first connecting block 21' is fixed on the front surface of the supporting unit 10' and a free end of the second block 22' is connected with the cantilever unit 30'. The cantilever unit 30' includes a cylinder 31' and a moving element 32' for pulling the plug element 2', and a force testing device 33' for reading the tension.

Usually, it needs to detect the tension in multi-direction to improve the completeness of a detecting data to better evaluate the performance and the lifetime of the plug element. Since the connecting unit 20' which is connected with the supporting unit 10' and the cantilever unit 30' is located in an immovable manner, the tensile testing device 1' is allowable to detect the tension in only one direction, which can not accurately evaluate the performance and the lifetime of the plug element. For improving the evaluation of the performance and the lifetime of the plug element, it needs several tensile testing devices 1' to detect the tension in multi-direction. In this way, the detecting cost is mounted.

SUMMARY OF THE INVENTION

It is an object of the present invention to provide a tensile testing device which can detect a tension in that a plug element is pulled out from a mating element in multi-direction. Another object of the present invention is to provide a tensile testing device which can save the detecting cost.

According to one aspect of the present invention, there is provided a tensile testing device, which is used for detecting an extracting force between a plug element and a mating element, includes a supporting unit, a connecting unit and a cantilever unit. The supporting unit is for securing mating elements thereon. The connecting unit includes a panel attached on a front surface of the supporting unit. An upper portion of the panel defines a first through hole and a plurality of eyelets around the first through hole to show a circle shape. A turning plate is pivoted to a front of the panel. The turning plate has a second through hole aligned with the first through hole, and a fixing aperture spaced from the second through hole. A first fixing pin is engaged in the fixing aperture and optional one of the eyelets for positioning the turned turning plate with respect to the panel. The cantilever unit for reading the tension is fixed on a front surface of the turning plate and has a lead which passes through the first and the second through holes to connect with the plug element which is coupled with one mating element. The cantilever unit is revolved on an axis of the second through hole to different positions accompanying with the turned turning plate, and drives the lead to pull the plug element so as to detect the extracting force between the plug element and the mating element from different directions.

According to another aspect of the present invention, there is provided a tensile testing device, which is used for detecting an extracting force between a plug element and a mating element, includes a supporting unit, a connecting unit and a cantilever unit. The supporting unit is for securing mating elements thereon. The connecting unit includes a first connecting block, a second connecting block and a second fixing pin. The first connecting block is of a lying u-shape and is installed on a front surface of the supporting unit. The first connecting block defines a slot between two facing boards thereof. One of the boards has a first positioning hole and a first location hole apart from the first positioning hole. The second connecting block defines a pivoted end which has a second positioning hole corresponding to the first positioning hole, and a plurality of second location holes around the second positioning hole. The second connecting block is pivotally held in the slot by a pin engaged the first positioning hole and the second positioning hole. The second fixing pin is engaged in the first location hole and optional one of the second location holes for making the second connecting block swing to different positions with respect to the first connecting block. The cantilever unit for reading the tension is connected to a fixing end of second connecting block and has a lead connecting with the plug element which is coupled with one mating element. The cantilever unit is revolved on an axis of the second positioning hole to different positions accompanying with the second connecting block, and drives the lead to pull the plug element so as to detect the extracting force between the plug element and the mating element from different directions.

According to another aspect of the present invention, there is provided a tensile testing device, which is used for detecting an extracting force between a plug element and a mating element, includes a supporting unit, a connecting unit and a cantilever unit. The supporting unit is for securing mating elements thereon. The connecting unit has a panel attached on a front surface of the supporting unit. An upper portion of the panel defines a first through hole and a plurality of eyelets around the first through hole to show a circle shape. A turning plate is pivoted to a front of the panel. The turning plate has a second through hole aligned with the first through hole, and a fixing aperture spaced from the second through hole. A first fixing pin is engaged in the fixing aperture and optional one of the eyelets for positioning the turned turning plate with respect to the panel. A first connecting block is installed on a front surface of the turning plate. The first connecting block is of a lying u-shape and defines a slot between two facing boards thereof. One of the boards has a first positioning hole and a first location hole apart from the first positioning hole. A second connecting block defines a pivoted end which has a second positioning hole corresponding to the first positioning hole, and a plurality of second location holes around the second positioning hole. The second connecting block is pivotally held in the slot by a pin engaged the first positioning hole and the second positioning hole. A second fixing pin is engaged in the first location hole and optional one of the second location holes for making the second connecting block swing to different positions with respect to the first connecting block. The cantilever unit for reading the tension is fixed on a fixing end of the second connecting block and has a lead which passes through the first and the second through holes to connect with the plug element which is coupled with one mating element. The cantilever unit is revolved on an axis of the second through hole to different positions accompanying with the turned turning plate and an axis of the second positioning hole to different positions accompanying with the second connecting block, and drives the lead to pull the plug element so as to detect the extracting force between the plug element and the mating element from different directions.

As the above description, the connecting unit of the tensile testing device can turn around the axis of the second through hole and the axis of the second positioning hole. Therefore, the cantilever unit connecting with the connecting unit can be driven to detect the tension in multi-direction. It saves detecting cost, and improves integrity of a detecting data to better evaluate the performance and the service life of the plug element.

BRIEF DESCRIPTION OF THE DRAWINGS

The present invention will be apparent to those skilled in the art by reading the following description of an embodiment thereof, with reference to the attached drawings, in which.

DETAILED DESCRIPTION OF THE EMBODIMENT

Figure 1:
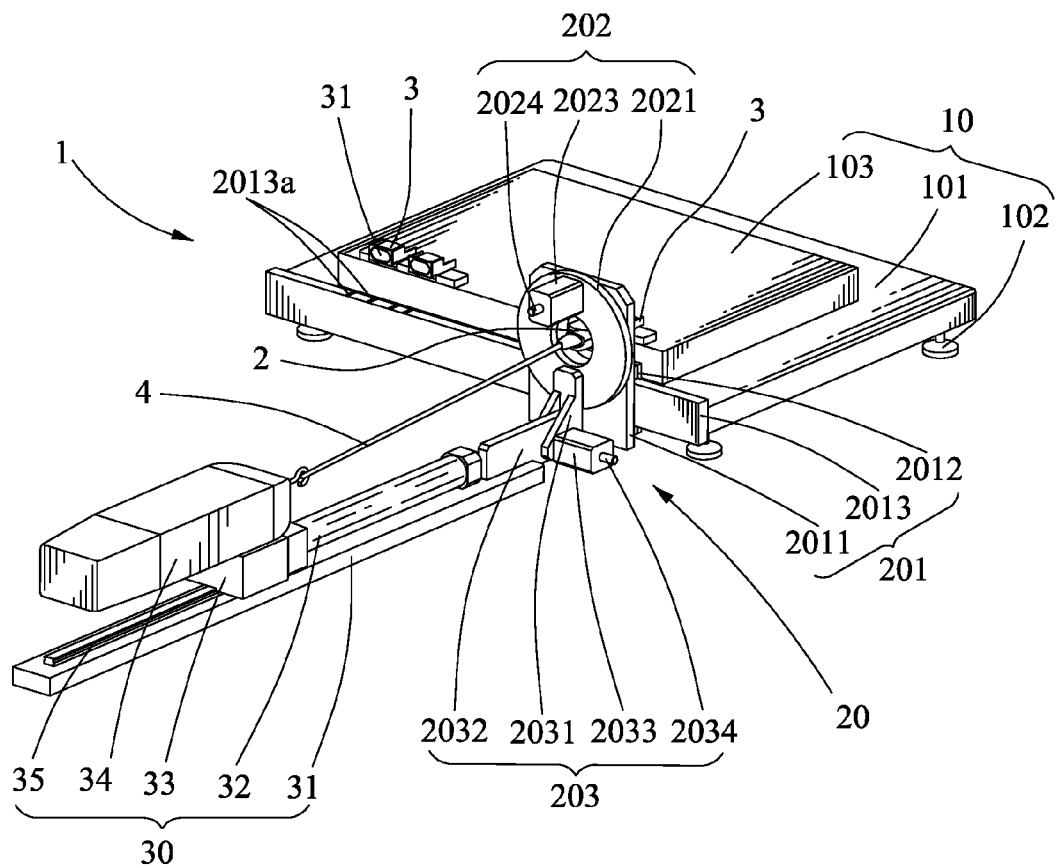
FIG. 1 is a perspective view of a tensile testing device of an embodiment according to the present invention.
Figure 2:
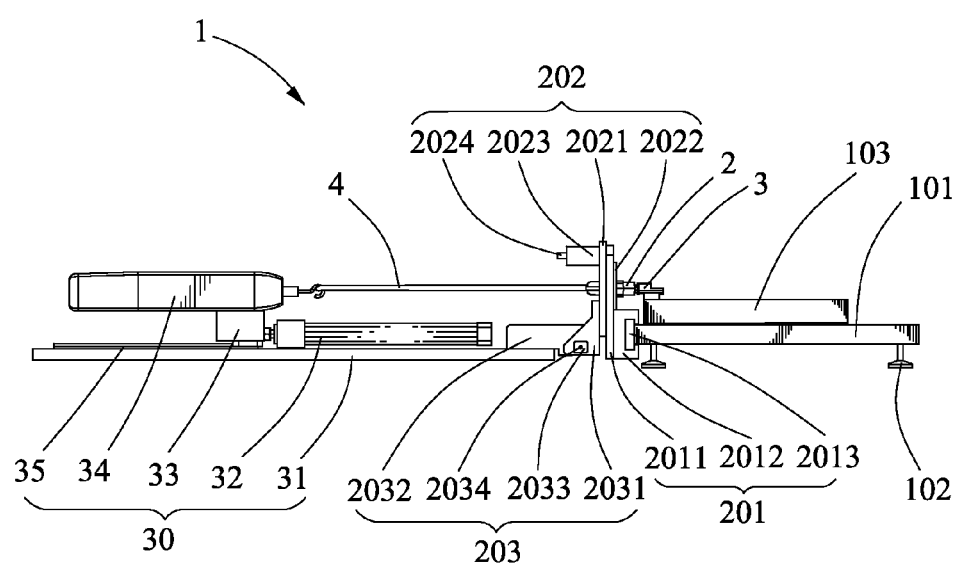
FIG. 2 is a right side view of the tensile testing device shown in FIG. 1.
Figure 3:
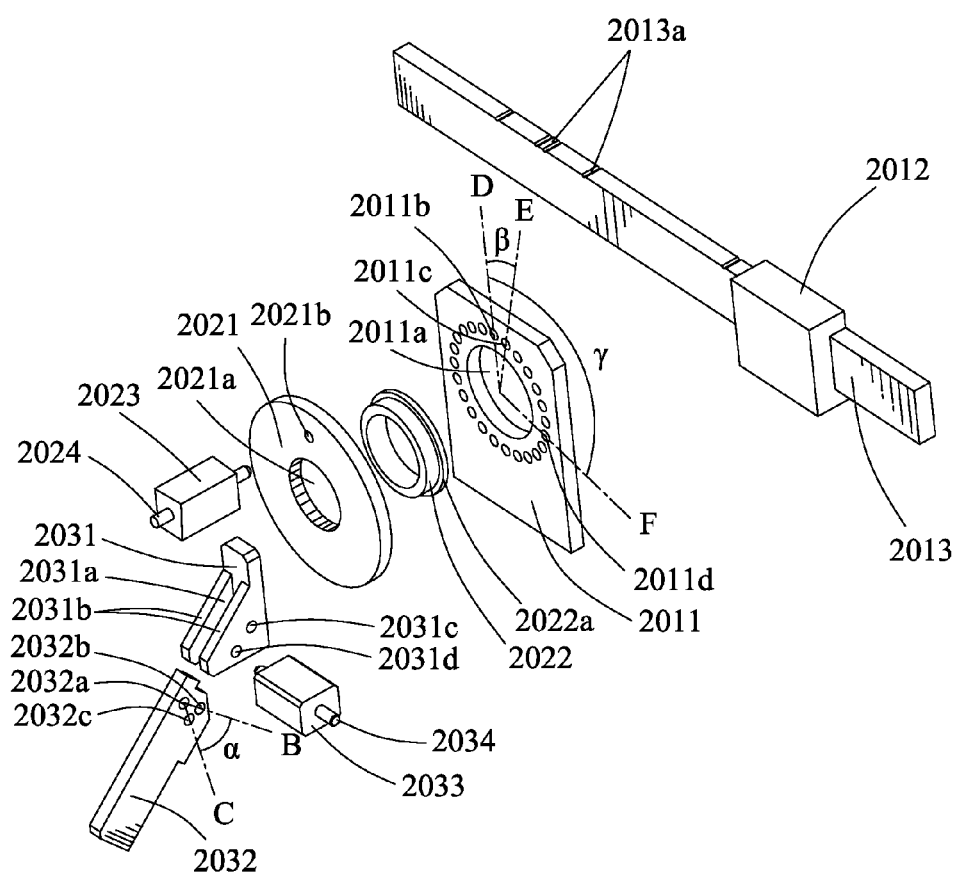
FIG. 3 is an exploded view of a connecting unit of the tensile testing device of FIG. 1.

Referring to FIGS. 1 to 3, a tensile testing device 1, which is used for detecting a tension in that a plug element 2 is pulled out from a mating element 3, includes a supporting unit 10, a connecting unit 20 and a cantilever unit 30. In this embodiment, the plug element 2 is a male connector, and the mating element 3 is a female connector. The supporting unit 10 includes a rectangle setting plate 101, with a plurality of legs 102 setting on a bottom surface thereof. A bolster plate 103 is fixed on a top surface of the setting plate 101 and is adjacent to a front surface of the setting plate 101. A plurality of mating elements 3 are arranged in a line along a front edge of a top surface of the bolster plate 103, with mating sockets 31 opening forward for mating with the plug element 2. One end of the connecting unit 20 is connected with the supporting unit 10 and can be turned around an axis which is perpendicular to the front surface of the setting plate 101, and the other end of the connecting unit 20 is connected with the cantilever unit 30 and can be turned around an axis, which is contained by a plane parallel with the front surface of the setting plate 101.

The cantilever unit 30 includes a base plate 31, a cylinder 32, a moving element 33 and a force testing device 34. The base plate 31 is a narrow plate and is fastened the connecting unit 20 at one end thereof. The other end of the base plate 31 has a slide way 35 on a top surface thereof. The cylinder 32 is installed on the top surface of the base plate 31 and is adjacent to the connecting unit 20. One end of the cylinder 32 is connected with the moving element 33 which slides along the slide way 35. The force testing device 34 is fixed on a top surface of the moving element 33. The plug element 2 is passed through the connecting unit 20 to mate with the mating element 3 at one end thereof, and the other end of the plug element 2 is connected with the force testing device 34 by a lead 4.

The connecting unit 20 includes a sliding element 201, a turning element 202 and a pivoted element 203. The sliding element 201 includes a substantial rectangle panel 2011 and a sliding block 2012 fixed on a lower portion of a rear surface of the panel 2011. An upper portion of the panel 2011 defines a first through hole 2011a in a middle portion thereof and a plurality of eyelets around the first through hole 2011a to show a circle shape. In this embodiment, the two adjacent eyelets are defined as 2011b, 2011c. A line D, which is defined with centers of the first through hole 2011a and the eyelet 2011b, and a line E, which is defined with centers of the first through hole 2011a and the eyelet 2011c, are formed with an angle β of 15 degrees therebetween. The sliding element 201 further includes a sliding rail 2013 attached to the front surface of the setting plate 101 and extending along the front edge of the top surface of the bolster plate 103. The sliding block 2012 can be slid along the sliding rail 2013, and is fastened at a predetermined position on the sliding rail 2013 by pits 2013a, which are defined on a top portion of the sliding rail 2013, for detecting the tension in that whether the plug element 2 is pulled out from different mating elements 3. The turning element 202 includes a turning plate 2021, a fixing sleeve 2022, a first fixing block 2023 and a first fixing pin 2024. The turning plate 2021 is of round shape and defines a second through hole 2021a in a middle portion thereof, and a fixing aperture 2021b corresponding to one of the eyelets. The fixing sleeve 2022 is short tube-shaped and defines a flange 2022a around periphery of one end thereof. One end of the fixing sleeve 2022 is fixed in the second through hole 2021a, the other end of the fixing sleeve 2022 is contained in the first through hole 2011a, with the flange 2022a being against to the rear surface of the panel 2011 to hold the turning plate 2021 with the panel 2011. So the turning plate 2021 could rotate with the fixing sleeve 2022 around an axis of the second through hole 2021a, and relative rotational movement could take place between the panel 2011 and the turning plate 2021. The first fixing block 2023 is of a rectangle shape, and has a pin hole extending through two opposite ends thereof. The first fixing pin 2024 is engaged in the pin hole of the first fixing block 2023, the fixing aperture 2021b and the eyelet 2011b in turn to secure the turning plate 2021 to the panel 2011. The pivoted element 203 includes a first connecting block 2031, a second connecting block 2032, a second fixing block 2033, and a second fixing pin 2034. The first connecting block 2031, which is secured to a portion of a front surface of the turning plate 2021 opposite to the fixing aperture 2021b, is substantially a lying u-shape and defines a slot 2031a between two facing boards 2031b thereof. One of the boards 2031b has a first positioning hole 2031c and a first location hole 2031d apart from the first positioning hole 2031c. The second connecting block 2032 is an elongated plate and defines a second positioning hole 2032a at an end thereof and two second location holes 2032b, 2032c around the second positioning hole 2032a. In this embodiment, a line B, which is defined with centers of the second positioning hole 2032a and the second location hole 2032b, and a line C, which is defined with centers of the second positioning hole 2032a and the second location hole 2032c, are formed with an angle α of 45 degrees therebetween. The second connecting block 2032 is pivotally held in the slot 2031a of the first connecting block 2031 by inserting a pin (not shown) through the first positioning hole 2031c and the second positioning hole 2032a in turn. The second fixing block 2033 has a structure similar to the first fixing block 2023 and defines a pin hole extending through two opposite ends thereof. The second fixing pin 2034 is engaged in the pin hole of the second fixing block 2033, the first location hole 2031d and the second location holes 2032b in turn to secure the second connecting block 2032 to the first connecting block 2031. Thus, the tension in that the plug element 2 being pulled out from the mating elements 3 in this direction will be detected.

Figure 4:
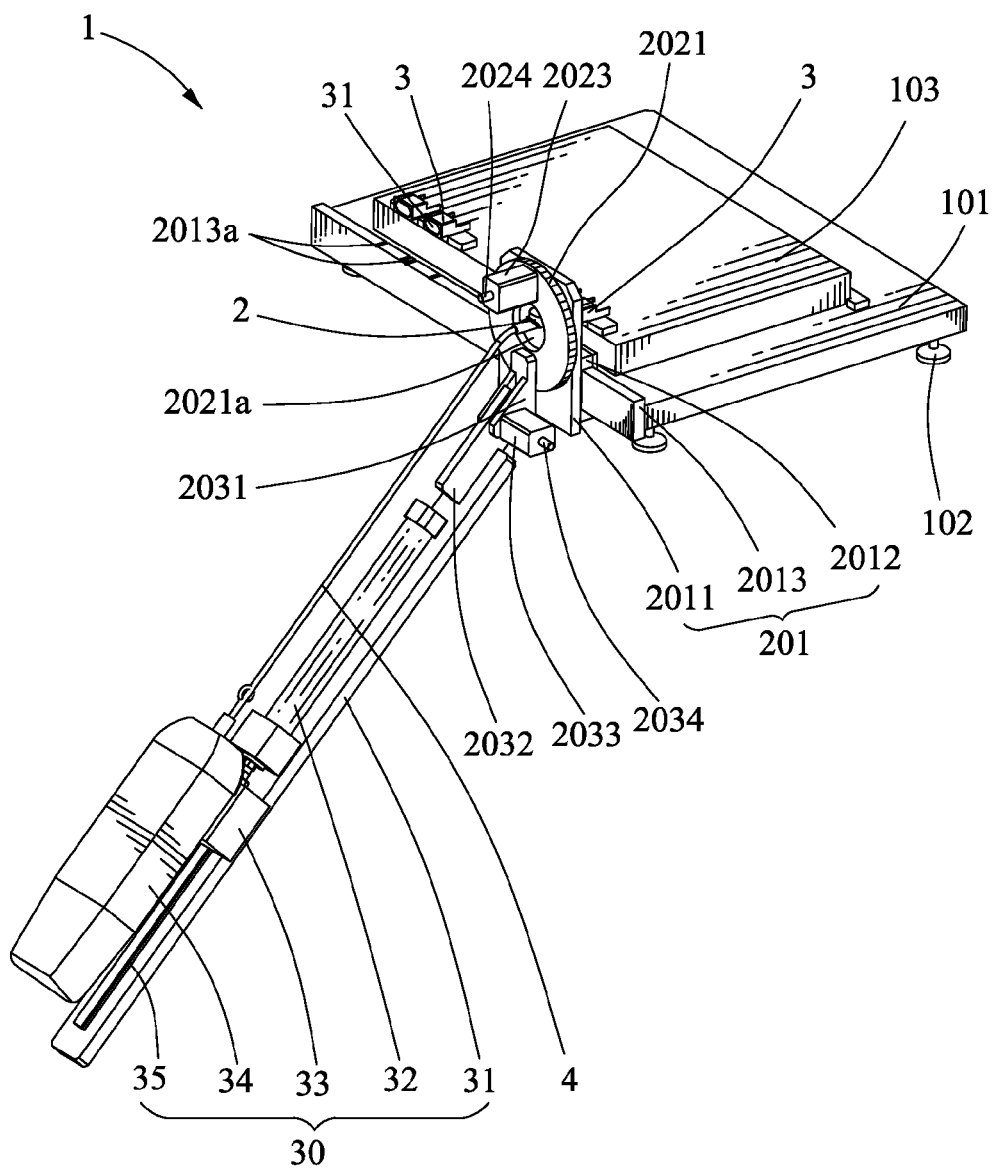
FIG. 4 is a perspective view to show a state that a cantilever unit of the tensile testing device of FIG. 1 turns 45 degrees counter-clockwise around an axis of a second positioning hole.
Figure 5:
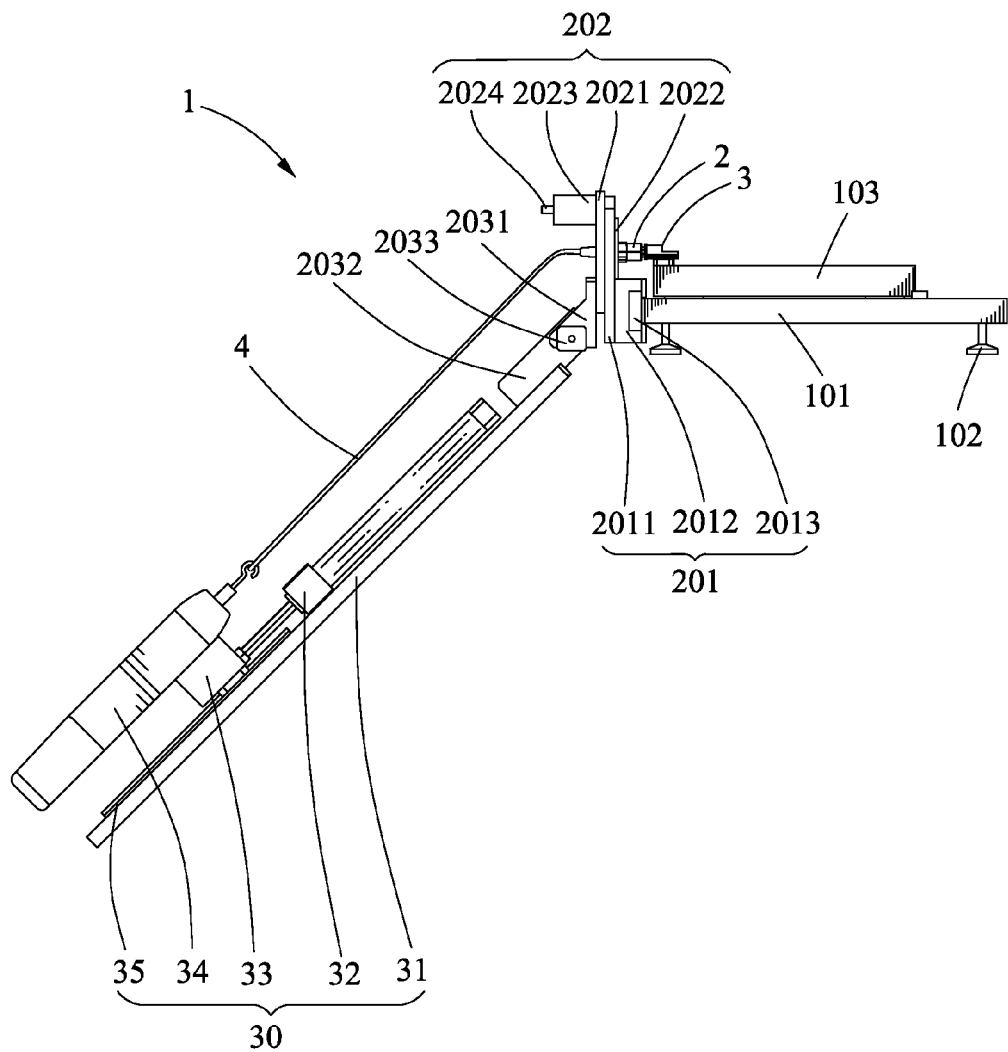
FIG. 5 is a right side elevational view of the tensile testing device shown in FIG. 4.

Please refer to FIGS. 4 and 5 in conjunction with FIG. 3, when the first fixing pin 2024 is still fixed in the eyelet 2011b, and the second fixing pin 2034 is fixed in the second location hole 2032c. The second connecting block 2032 is turned 45 degrees counter-clockwise around an axis of the second positioning hole 2032a. Therefore, the cantilever unit 30, which is connecting the second connecting block 2032, can turn 45 degrees counter-clockwise around the axis of the second positioning hole 2032a relative to the cantilever unit 30 of FIG. 1. Thus, the tension in that the plug element 2 being pulled out from the mating elements 3 at this direction will be detected.

Figure 6:
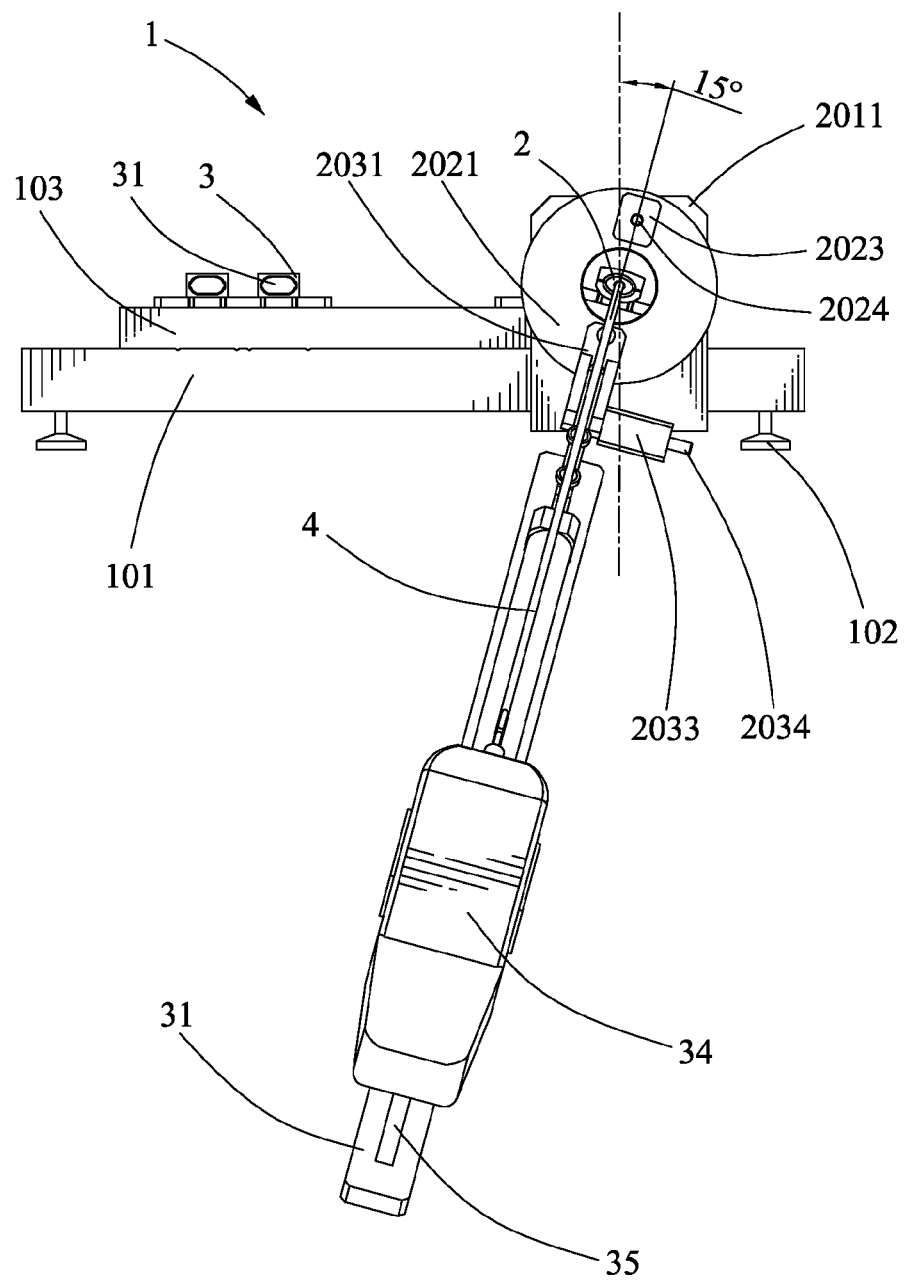
FIG. 6 is a perspective view to show a state that the cantilever unit of the tensile testing device of FIG. 4 turns 15 degrees clockwise around an axis of a second through hole.

Please refer to FIG. 6 in conjunction with FIG. 3, when the second fixing pin 2034 is fixed in the second location hole 2032c, and the first fixing pin 2024 is fixed in the eyelet 2011c. The pivoted element 203 is turned 15 degrees clockwise around the axis of the second through hole 2021a with the turning plate 2021 relative to the pivoted element 203 of FIG. 4. Therefore, when the first fixing pin 2024 is fixed in the eyelet 2011c, the cantilever unit 30 can turn 15 degrees clockwise around the axis of the second through hole 2021a relative to the cantilever unit 30 of FIG. 4. Thus, the tension in that the plug element 2 being pulled out from the mating elements 3 at this direction will be detected.

Figure 7:
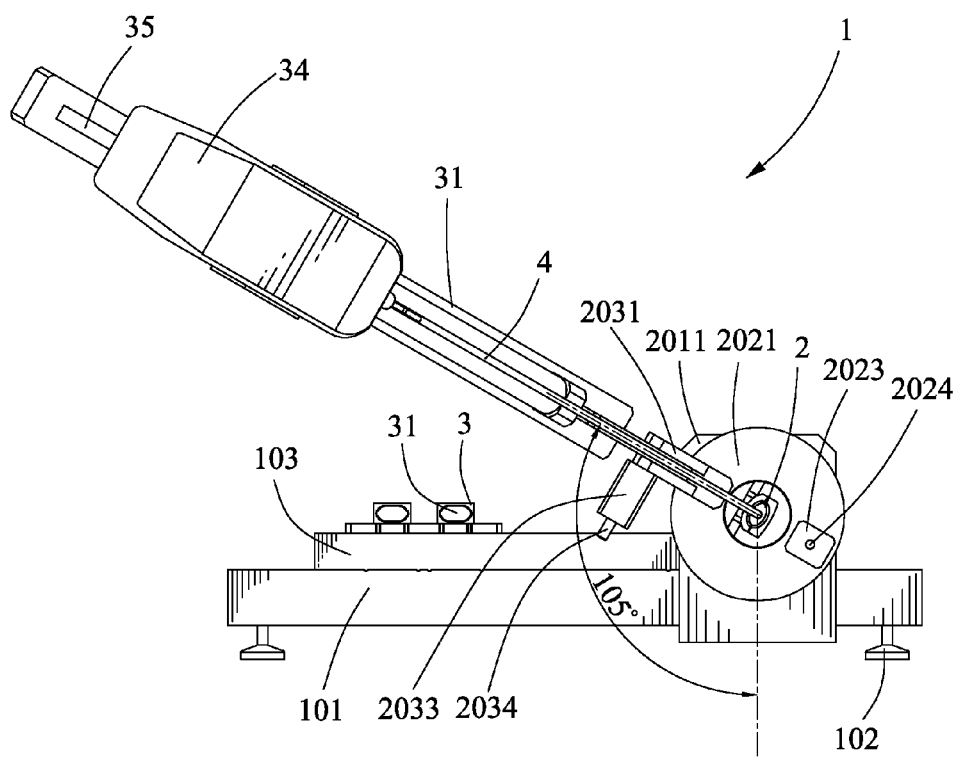
FIG. 7 is a perspective view to show a state that the cantilever unit of the tensile testing device of FIG. 4 turns 105 degrees clockwise around the axis of a second through hole.
Figure 8:
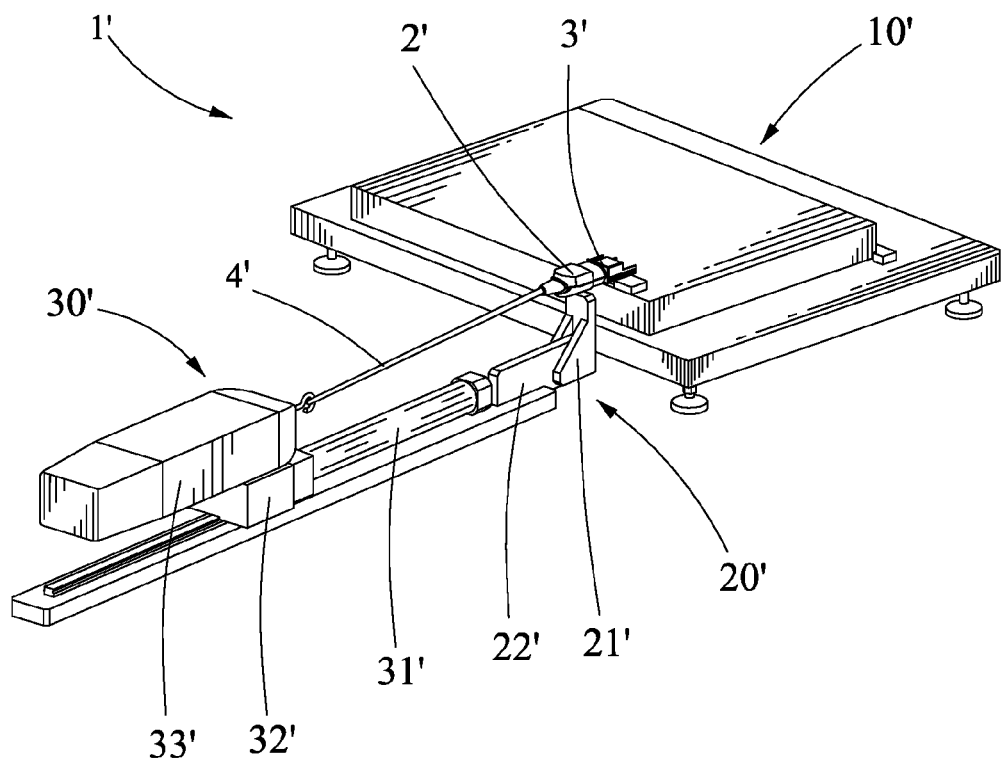
FIG. 8 is a perspective view of a conventional tensile testing device.

Please refer to FIG. 7 in conjunction with FIG. 3, when the second fixing pin 2034 is fixed in the second location hole 2032c, and the first fixing pin 2024 is fixed in the eyelet designated as 2011d. A line F, which is defined with centers of the first through hole 2011a and the eyelet 2011d, and the line D are formed with an angle γ of 105 degrees. The pivoted element 203 is turned 105 degrees clockwise around the axis of the second through hole 2021a with the turning plate 2021 relative to the pivoted element 203 of FIG. 4. Therefore, when the first fixing pin 2024 is fixed in the eyelet 2011d, the cantilever unit 30 can turn 105 degrees clockwise around the axis of the second through hole 2021a relative to the cantilever unit 30 of FIG. 4. Thus, the tension in that the plug element 2 being pulled out from the mating elements 3 at this direction will be detected.

Furthermore, in this embodiment, the tensile testing device includes a speed governor valve (not shown) to control a speed of the cylinder 32.

When the tension detected, the connecting unit 20 together with the cantilever unit 30 are slid to the predetermined position to align the mating elements 3 which is going to be detected with. The plug element 2 is passed through the second through hole 2021b and the first through hole 2011a to mate with the mating element 3. The lead 4 connecting the plug element 2 is fastened to the force testing device 34, and the speed governor valve (not shown) is adjusted to control the speed of the cylinder 32. When the cylinder 32 is drove, the moving element 33 is pushed by the cylinder 32 to slide along the slide way 35 to take the force testing device 34 moving slowly along the slide way 35. When the plug element 2 is departed from the mating element 3, a reading on the force testing device 34 shows the tension when pull out the plug element 2 from the mating element 3.

As described above, the connecting unit 20 of the tensile testing device 1 can slide along the sliding rail 2013, and turn around the axis of the second through hole 2021a and the axis of the second positioning hole 2032a. Therefore, the cantilever unit 30 can be driven to slide along the sliding rail 2013, turn around the axis of the second through hole 2021a and the axis of the second positioning hole 2032a. So the tension can be measured from multi-direction. It saves detecting cost, and improves completeness of a detecting data to better evaluate the performance and the lifetime of the plug element.

What is claimed is:

1. A tensile testing device, which is used for detecting an extracting force between a plug element and a mating element, comprising:
a supporting unit for securing mating elements thereon;
a connecting unit including a panel attached on a front surface of the supporting unit, an upper portion of the panel defining a first through hole and a plurality of eyelets around the first through hole to show a circle shape, a turning plate pivoted to a front of the panel, the turning plate having a second through hole aligned with the first through hole, a fixing aperture spaced from the second through hole, a first fixing pin engaged in the fixing aperture and optional one of the eyelets for positioning the turned turning plate with respect to the panel; and
a cantilever unit for reading the tension fixed on a front surface of the turning plate, the cantilever unit having a lead which passes through the first and the second through holes to connect with the plug element which is coupled with one mating element,
wherein the cantilever unit is revolved on an axis of the second through hole to different positions accompanying with the turned turning plate, and drives the lead to pull the plug element so as to detect the extracting force between the plug element and the mating element from different directions.

2. The tensile testing device as claimed in claim 1, wherein the turning plate is pivoted to the front of the panel by a tube-shaped fixing sleeve, the fixing sleeve has a fixed end and a pivoted end with a flange protruding around a periphery thereof, the fixed end is fixed in the second through hole, and the pivoted end is contained in the first through hole, with the flange being against a rear surface of the panel to hold the turning plate with the panel.

3. The tensile testing device as claimed in claim 1, wherein the connecting unit further includes a pivoted element for pivotally connecting the cantilever unit with the turning plate and enabling the cantilever unit to turn around an axis, which is perpendicular to the axis of the second through hole.

4. The tensile testing device as claimed in claim 3, wherein the pivoted element has a first connecting block fastened to the front surface of the turning plate, and a second connecting block having a pivoted end connected with the first connecting block and a fixing end fixed to the cantilever unit, the first connecting block is substantially a lying u-shape and defines a slot between two facing boards thereof for receiving the pivoted end, one of the boards has a first positioning hole and a first location hole apart from the first positioning hole, the pivoted end of the second connecting block defines a second positioning hole corresponding to the first positioning hole, and two second location holes around the second positioning hole, the first location hole is alternatively positioned to one of the second location holes.

5. The tensile testing device as claimed in claim 4, wherein a line, which is defined with centers of the second positioning hole and one of the second location holes, and a line, which is defined with centers of the second positioning hole and the other one of the second location hole, are formed with an angle of 45 degrees therebetween.

6. The tensile testing device as claimed in claim 1, wherein a line, which is defined with centers of the first through hole and one of the eyelet, and a line, which is defined with centers of the first through hole and an adjacent eyelet, are formed with an angle of 15 degrees.

7. The tensile testing device as claimed in claim 1, wherein the connecting unit further includes a sliding rail attached on a front surface of the supporting unit and extending along a top edge of the front surface of the supporting unit, and a sliding block fixed on a lower portion of a rear surface of the panel and sliding on the sliding rail for aligning the cantilever unit to the mating element which is going to be detected with.

8. The tensile testing device as claimed in claim 7, wherein the sliding rail defines a plurality of pits on a top portion thereof to fasten sliding block at a predetermined position.

9. A tensile testing device, which is used for detecting an extracting force between a plug element and a mating element, comprising:
   a supporting unit for securing mating elements thereon;
   a connecting unit including a first connecting block installed on a front surface of the supporting unit and a second connecting block, the first connecting block being of a lying u-shape and defining a slot between two facing boards thereof, one of the boards having a first positioning hole and a first location hole apart from the first positioning hole, the second connecting block defining a pivoted end which has a second positioning hole corresponding to the first positioning hole, and a plurality of second location holes around the second positioning hole, the second connecting block pivotally held in the slot by a pin engaged the first positioning hole and the second positioning hole, a second fixing pin engaged in the first location hole and optional one of the second location holes for making the second connecting block swing to different positions with respect to the first connecting block; and
   a cantilever unit for reading the tension fixed on a fixing end of the second connecting block and having a lead connecting with the plug element which is coupled with one mating element,
   wherein the cantilever unit is revolved on an axis of the second positioning hole to different positions accompanying with the second connecting block, and drives the lead to pull the plug element so as to detect the extracting force between the plug element and the mating element from different directions.

10. The tensile testing device as claimed in claim 9, wherein the connecting unit further includes a panel and a turning plate for pivotally connecting the first connecting block with the supporting unit, and enabling the first connecting block to rotate around an axis which is perpendicular to the axis of the second positioning hole.

11. The tensile testing device as claimed in claim 10, wherein the panel is attached on a front surface of the supporting unit, an upper portion of the panel defines a first through hole and a plurality of eyelets are arranged around the first through hole to show a circle shape, the turning plate is pivoted to a front of the panel and has a second through hole aligned with the first through hole, a fixing aperture is spaced from the second through hole, a first fixing pin is engaged in the fixing aperture and optional one of the eyelets for positioning the turned turning plate with respect to the panel, the first connecting block fixed on a front surface of the turning plate and enabled to rotate with the turning plate around an axis of the second through hole.

12. The tensile testing device as claimed in claim 11, wherein the turning plate is pivoted to the front of the panel by a tube-shaped fixing sleeve, the fixing sleeve has a fixed end and a pivoted end with a flange protruding around a periphery thereof, the fixed end is fixed in the second through hole, and the pivoted end is contained in the first through hole, with the flange being against a rear surface of the panel to hold the turning plate with the panel.

13. The tensile testing device as claimed in claim 12, wherein a line, which is defined with centers of the first through hole and one of the eyelet, and a line, which is defined with centers of the first through hole and an adjacent eyelet, are formed with an angle of 15 degrees.

14. The tensile testing device as claimed in claim 13, wherein the connecting unit further includes a sliding rail attached on the front surface of the supporting unit and extending along a top edge of the front surface, and a sliding block fixed on a lower portion of the rear surface of the panel and sliding on the sliding rail for aligning the cantilever unit to the mating element which is going to be tested with.

15. The tensile testing device as claimed in claim 14, wherein the sliding rail defines a plurality of pits on a top portion thereof to fasten sliding block at a predetermined position.

16. The tensile testing device as claimed in claim 9, wherein a line, which is defined with centers of the second positioning hole and one of the second location holes, and a line, which is defined with centers of the second positioning hole and an adjacent one of the second location hole, are formed with an angle of 45 degrees.

17. A tensile testing device, which is used for detecting an extracting force between a plug element and a mating element, comprising:
   a supporting unit for securing mating elements thereon;
   a connecting unit including:
      a panel attached on a front surface of the supporting unit, an upper portion of the panel defining a first through hole and a plurality of eyelets around the first through hole to show a circle shape;
      a turning plate pivoted to a front of the panel, the turning plate having a second through hole aligned with the first through hole, a fixing aperture spaced from the second through hole;
      a first fixing pin engaged in the fixing aperture and optional one of the eyelets for positioning the turned turning plate with respect to the panel;
      a first connecting block installed on a front surface of the turning plate, the first connecting block being of a lying u-shape and defining a slot between two facing boards thereof, one of the boards having a first positioning hole and a first location hole apart from the first positioning hole;
      a second connecting block defining a pivoted end which has a second positioning hole corresponding to the first positioning hole, and a plurality of second location holes around the second positioning hole, the second connecting block pivotally held in the slot by a pin engaged the first positioning hole and the second positioning hole; and a second fixing pin engaged in the first location hole and optional one of the second location holes for making the second connecting block swing to different positions with respect to the first connecting block; and a cantilever unit for reading the tension fixed on a fixing end of the second connecting block, the cantilever unit having a lead which passes through the first and the second through holes to connect with the plug element which is coupled with one mating element, wherein the cantilever unit is revolved on an axis of the second through hole to different positions accompanying with the turned turning plate and an axis of the second positioning hole to different positions accompanying with the second connecting block, and drives the lead to pull the plug element so as to detect the extracting force between the plug element and the mating element from different directions.

* * * * *